(12) United States Patent
Zanotto et al.

(10) Patent No.: US 9,731,994 B2
(45) Date of Patent: Aug. 15, 2017

(54) VITREOUS COMPOSITION, BIOACTIVE VITREOUS FIBERS AND FABRICS, AND ARTICLES

(71) Applicant: Fundação Universidade Federal De São Carlos, São Carlos (BR)

(72) Inventors: Edgar Dutra Zanotto, São Carlos (BR); Oscar Peitl Filho, São Carlos (BR); Marina Trevelin Souza, São Carlos (BR)

(73) Assignee: Fundação Universidade Federal De São Carlos, São Carlos (BR)

( * ) Notice: Subject to any disclaimer, the term of this patent is extended or adjusted under 35 U.S.C. 154(b) by 28 days.

(21) Appl. No.: 14/911,444

(22) PCT Filed: Aug. 12, 2014

(86) PCT No.: PCT/BR2014/000275
§ 371 (c)(1),
(2) Date: Feb. 10, 2016

(87) PCT Pub. No.: WO2015/021519
PCT Pub. Date: Feb. 19, 2015

(65) Prior Publication Data
US 2016/0184475 A1   Jun. 30, 2016

(30) Foreign Application Priority Data

Aug. 12, 2013  (BR) .......................... 1020130209619

(51) Int. Cl.
| | | |
|---|---|---|
| C03C 3/097 | (2006.01) |
| C03C 13/00 | (2006.01) |
| C03C 25/24 | (2006.01) |
| A61L 27/10 | (2006.01) |
| C03B 37/02 | (2006.01) |
| C03C 25/12 | (2006.01) |
| C03C 25/10 | (2006.01) |
| A61L 27/56 | (2006.01) |
| A61K 33/08 | (2006.01) |
| A61L 27/34 | (2006.01) |
| A61L 27/54 | (2006.01) |
| C03C 4/00 | (2006.01) |
| C03C 12/00 | (2006.01) |
| A61L 27/12 | (2006.01) |
| A61L 27/58 | (2006.01) |
| C03B 19/01 | (2006.01) |
| A61K 33/22 | (2006.01) |
| A61K 33/38 | (2006.01) |
| A61K 33/42 | (2006.01) |
| B33Y 10/00 | (2015.01) |
| B33Y 80/00 | (2015.01) |

(52) U.S. Cl.
CPC .............. *C03C 3/097* (2013.01); *A61K 33/08* (2013.01); *A61L 27/10* (2013.01); *A61L 27/12* (2013.01); *A61L 27/34* (2013.01); *A61L 27/54* (2013.01); *A61L 27/56* (2013.01); *A61L 27/58* (2013.01); *C03B 19/01* (2013.01); *C03B 37/02* (2013.01); *C03C 4/0007* (2013.01); *C03C 4/0014* (2013.01); *C03C 4/0021* (2013.01); *C03C 12/00* (2013.01); *C03C 13/00* (2013.01); *C03C 25/10* (2013.01); *C03C 25/12* (2013.01); *C03C 25/24* (2013.01); *A61K 33/22* (2013.01); *A61K 33/38* (2013.01); *A61K 33/42* (2013.01); *A61L 2300/404* (2013.01); *A61L 2300/412* (2013.01); *A61L 2400/18* (2013.01); *A61L 2420/02* (2013.01); *A61L 2430/02* (2013.01); *B33Y 10/00* (2014.12); *B33Y 80/00* (2014.12); *C03C 2204/02* (2013.01); *C03C 2213/02* (2013.01)

(58) Field of Classification Search
None
See application file for complete search history.

(56) References Cited

U.S. PATENT DOCUMENTS

| 2004/0151745 A1 | 8/2004 | Zimmer et al. |
| 2008/0044488 A1 | 2/2008 | Zimmer et al. |
| 2009/0208428 A1 | 8/2009 | Hill et al. |

FOREIGN PATENT DOCUMENTS

WO   2004074199 A1   9/2004

OTHER PUBLICATIONS

International Search Report in related PCT Application No. PCT/BR2014/000275, dated completed Sep. 5, 2014.
Written Opinion in related PCT Application No. PCT/BR2014/000275, dated completed Sep. 5, 2014.

*Primary Examiner* — Elizabeth A Bolden
(74) *Attorney, Agent, or Firm* — Troutman Sanders, LLP; Ryan A. Schneider

(57) ABSTRACT

A vitreous composition according to Table (I) is described. Continuous vitreous fibers are obtained by downdrawing said molten composition, with a length ranging from millimeters to kilometers and diameters ranging from 2 μm to 3 mm. The fibers are covered with collagen and form vitreous fabrics. The fabrics form articles with a variety of medical uses.

22 Claims, 12 Drawing Sheets a) A-2 weeks w/o graft/B-4 weeks w/o graft  b) A-2 weeks with graft/B- 4 weeks with graft
C-8 weeks w/o graft/ D-16 weeks w/o graft    C-8 weeks with graft/ D-16 weeks with graft

VITREOUS COMPOSITION, BIOACTIVE VITREOUS FIBERS AND FABRICS, AND ARTICLES

FIELD OF THE INVENTION

This invention belongs to the field of vitreous compositions and bioactive tissues, which can be obtained from said compositions, more specifically, to a composition for obtaining highly bioactive vitreous fabrics and to articles for medical and dental applications manufactured with such vitreous fabrics.

BACKGROUND OF THE INVENTION

Over the last decades, health researchers and professionals have been searching for a material that may be applied as an alloplastic graft which, as well as integrating with the tissue to be replaced, may also induce regeneration of the damaged tissue and be reabsorbed at the same rate in which the new tissue is formed, these materials being recently classified as third generation biomaterials.

Ceramic materials have been performing well in this field of biological application and are widely studied due to high biocompatibility and osteoconductive properties.

Currently, there is a wide variety of vitreous material or bioactive or biocompatible ceramics, such as dental ceramics, granular or scaffold-shaped bone grafts for bone replacement, etc. Its clinical applications include repair of hard tissue such as bones, teeth, and eventually soft tissue, see Hench, L. L; Wilson, J. *An Introduction to Bioceramics. Advanced Series in Ceramics*. Singapore: World Scientific Publishing Ltd., 993.

Among the most commonly used materials for the aforementioned applications, bioactive glasses have become increasingly requested due to higher bioactivity and, therefore, advantageous when compared to other materials applied as synthetic grafts (also known as alloplastic grafts).

These glasses are part of a class of biomaterials based on vitreous silicate compounds, according to the article by Cerruti, M. G. et al. *An analytical model for the dissolution of different particle size samples of Bioglass in TRIS-buffered solution*. Biomaterials, v. 26, p. 4903-4911, 2005, which have excellent bioactive and osteoconductive properties; see related article by Oonishi et al., *Particulate bioglass compared with hydroxyapatite as a bone graft substitute*. Clin Orthop Relat Res, p. 316-325, 1997. They were developed by Hench, L. L. and collaborators in the early 1970s, according to the quote above and, ever since, the behavior of these materials and the many possible bioactive compositions are studied.

However, for in vivo applications, this material has been limited only to small monolithic parts, to particulate and granules or rigid scaffolds, which prevent its application in all clinical cases, since the choice of the bone grafting to be used depends on many factors such as size of the defect, number of surrounding walls, etc. This happens because the vast majority of bioactive vitreous compositions developed thus far have a high crystallization tendency, and thus, a thermal treatment process is not feasible. Therefore, the development of new vitreous compositions capable of withstanding heating/cooling treatments without loss of vitreous phase and bioactive characteristics is extremely recent and important.

With these different processes, it is possible to obtain fibers that may lead to bioactive meshes, fabrics, scaffolds or curatives. This also represents a very promising advancement for alloplastic materials, as it further broadens the range of utilization of bioactive glasses and enables its use in cases when one or more types of osteoconductive and/or osteoinductive materials are needed.

The development of fibers and fabrics from this type of biomaterial would enable the creation of grafts extremely reactive to body fluids, of easier handling, adjustable to the bone cavity and with good mechanical properties.

Bioactive glasses may feature a very broad field of application when presented as fibers, meshes and fabrics. This type of conformity may find its main use as a synthetic graft (alloplastic), acting as a guide for the new formation of soft and/or hard tissue.

In dentistry, for example, these vitreous fiber meshes or fabrics may be used as reinforcements in periodontal surgery, surgical procedures for increase of bone volume of the alveolar ridge for periodontal surgery, surgical procedures for increase of bone volume of the alveolar ridge to enable rehabilitation with implants, maxillary sinus augmentation, etc.; and in medicine these fabrics could be used in general orthopedic surgery, fractures, craniofacial deformities and general soft tissue regeneration.

The bioactive glass fiber fabrics and meshes may also be able to replace titanium meshes (FIG. 1), which are widely used nowadays in fracture surgery which involve orbital floor (blow-out eye region fractures), see Pinto, J. G. S. et al. *Enxerto autógeno x biomateriais no tratamento de fraturas e deformidades faciais-uma revisão de conceitos atuais*. RFO, v. 12, p. 79-84, 2007, and also associated to particulate autogenous bone grafts or allografts for maintenance and stabilization in the desired location, as mentioned in Cortez, A. L. V. et al., *Reconstrução de Maxila Atrófica utilizando Osso Autogéneo e Malha de Titânio para Posterior Reabilitação com Implantes-Caso Clinico*. Revista Portuguesa de Estomatologia, Medicina Dentária e Cirurgia Maxilofacial, v. 45, p. 163-167, 2004.

Other recently discovered fields of application for bioactive fibers are: use in dermatological wounds and ulcerations, such as varicose ulcers and/or skin wounds due to chronic diseases, such as diabetes, which take long periods to heal or even are unable to fully heal on its own.

However, the majority of bioactive glass compositions developed thus far feature a high crystallization tendency and a very limited working range, according to U.S. Pat. No. 6,054,400, since it normally has great amounts of alkaline and alkaline earth (R). These elements are considered structure modifiers, as they create non-bridging oxygens (—Si—O—R) and smaller structural units; this causes vitreous compositions to be more susceptible to crystallization, since the energy released by the heating during the fiber manufacturing processes is enough to cause rupture of chemical bonds, which are weaker than bridging Si—O—Si bonds, thus enabling atom rearrangement and subsequent devitrification, see Arstila, H. et al. *Factors affecting crystallization of bioactive glasses*. Journal of the European Ceramic Society, v. 27, p. 1543-1546, 2007.

Another behavior of this type of vitreous formulation, which tends to affect the fabrication of fibers, is a viscous behavior characterized by rapid change with little temperature variations, that is, these glasses are known as "fragile" glass compositions, as mentioned in the article by Arstla, H. et al., above.

Therefore, these materials in general cannot be manufactured via conventional methods, such as the downdrawing process, and for this reason, the fibers obtained with traditional bioactive vitreous compositions are currently made mostly through the melt spinning process. Nevertheless, this technique is only capable of producing small fibers or extremely thin strip-shaped samples, see /Melt_spinning; http://en.wikipedia.org/wiki.

The vitreous compositions most commonly known for obtaining fibers through this process are: 13-93 and 9-93 glasses, and this is possible because both formulations have a significantly higher amount of silica in relation to standard bioactive vitreous compositions, with 53 wt % and 54 wt %, respectively; while the Bioglass® 45S5 has approximately 45 wt %, as mentioned in the articles by Pirhonen, E. et al. *Manufacturing, Mechanical Characterization, and In vitro Performance of Bioactive Glass* 13-93 *Fibers*. Wiley InterScience, 2005. IOD: 10.1002/jbm.b.30429 and Pirhonen, E, et al. *Mechanical Properties of Bioactive Glass 9-93 Fibers*. Acta Biomaterial, v. 2, p. 103-107, 2006.

This represents a major stability gain regarding the crystallization phenomenon, since silica is considered a glass former element. However, this broader working range of the bioactive 13-93 glass that allows creation of fibers leads to a kinetic of slower superficial reactions than the Bioglass 45S5. This glass takes approximately seven days in a SBF-K9 solution for the formation of the carbonated hydroxyapatite (HCA) layer, while for the Bioglass® this takes place in 6 to 8 hours, see the book by Pirhonen, E. et al. *Manufacturing, Mechanical Characterization, and In vitro Performance of Bioactive Glass 13-93 Fibers*. Wiley InterScience, 2005. DOI: 10.1002/jbm.b.30429 and Hench, L. L. Bioceramics: *From Concept to Clinic*. Journal of the American Ceramic Society, v. 74, p. 1487-1510, 1991.

Another process of fiber obtainment that has been studied is electrospinning. This technique needs the use of the sol-gel process to obtain vitreous material and, therefore, is much more expensive than the downdrawing technique, as well as being used, preferably, for obtaining submicron fibers for porous scaffolds fabrication, see Lu, H. et al. *Electrospun submicron bioactive glass fibers for bone tissue scaffold*. J Mater Sei: Mater Med, v. 20, p. 793-798, 2009 and Hong, Y. et al. *Tissueation and Drug Delivery of Ultrathin Mesoporous Bioactive Glass Hollow Fibers*. Adv. Funct. Mater, v. 20, p. 1503-1510, 2010. Thus, fiber production through the downdrawing method brings advantages such as production of continuous fibers of varied and controlled diameters and a less expensive process than the aforementioned techniques.

Regarding cellular interaction and response, a wide variety of cells may be grown over fibers or meshes, as their open structures facilitate growth of the desired organic tissue and improve the diffusion process of nutrients and excreta coming from said cells, Clupper, D. C. et al. *Bioactive Evaluation of 45S5 bioactive glass fibers and Preliminary Study of Human Osteoblast Attachment*. J. Mat Science: Materials in Medicine, v. 15, p. 803-808, 2004, which enables rapid healing of bone injuries and defects.

In the study of Clupper, D. C. et al. a rapid interaction was observed between bone cells (osteoblasts) and the surface of the hand-pulled fibers from glass 45S5; after fifteen minute, the cells had already adhered to the material, and their number grew over time.

Brown, R. F. et al. *Growth and differentiation of osteoblastic cells on 13-93 bioactive glass fibers and scaffolds*, Acta Biomaterialia, v. 4, p. 387-396, 2008 have proved that scaffolds obtained via 13-93 glass fibers have combined properties that improve deposition, bonding, differentiation and growth of osteoblasts on the biomaterial.

Moimas L. et al. *Rabbit pilot study on the resorbability of three-dimensional bioactive glass fiber scaffolds*, Acta Biomaterialia, v. 2, p. 191-199, 2006 verified in a preliminary study that scaffolds made of fibers obtained through melt spinning, when implanted in bone defects in rabbits, have shown full resorption capacity in 6 months and attained good results regarding repair and remodeling of the bone defect.

Regarding mechanical properties of the fibers, Clupper, D. C. et al. have demonstrated that tensile strength of 45S5 glass fibers, with average diameter of 79 μm, was of 340±140 MPa, which corroborates with other studies, such as Diego L. et al., *Tensile Properties of Bioactive Fibers for Tissue Engineering Applications*. J. Biomed. Mater. Res., v. 53, p. 199, 2000, which showed a 200 and 150 MPa tensile strength for 45S5 fibers of 200 and 300 μm, respectively. These studies show that fiber mechanical properties is correspondent to its diameter and, thus, the thinner the fiber, the more resistant it will be.

In this way, the use of vitreous formulations which combine properties such as: a rapid interaction with body fluids, that is, a high bioactivity, and higher glass stability, with a broad working range, enable obtaining fibers through the downdrawing process.

The downdrawing process is largely used for production of glass fibers in industrial scale, but for existing bioactive vitreous compositions up to now, this type of processing is not feasible, since they have low glass stability and normally a highly uncontrolled crystallization generating the degradation of its mechanical and bioactive properties, which in turn leads to quick rupture of the fibers, affecting or even hindering the fabrication of continuous fibers.

Therefore, for the manufacture of bioactive fibers, currently more expensive and complex processes are needed, such as melt spinning, electrospinning and laser spinning. Although, these processes only yield small fiber pieces, that is, these are not continuous fibers such as the ones obtained through downdrawing.

The lack of perspective and the high cost associated to these other techniques restrict the clinical utilization of these powdered or particulate biomaterials, thus the development of a new vitreous formulation, which enables manufacturing of continuous fibers and, subsequently, highly bioactive meshes and fabrics is distinctly innovative.

On the other hand, the compositions developed so far only allow manufacturing of devices, which do not need late thermal treatment, since the thermal energy generated on these processes is enough for rearrangement of the atoms of the glass into crystals; therefore, the industry of bioactive glasses is restricted to manufacturing powders and granulates.

The patent literature also presents documents pertinent to the study of bioactive glasses.

Thus, U.S. Pat. No. 6,517,857B2 describes a bioactive glass fiber mesh obtained from two distinct vitreous compositions, one with higher bioactivity and the other with less bioactivity. The main composition range informed is of 6 wt % of $Na_2O$, 12 wt % of $K_2O$, 5 wt % of MgO, 20 wt % of CaO, 4 wt % of $P_2O_5$ and 53 wt % of $SiO_2$ for the most bioactive vitreous composition, and 6 wt % of $Na_2O$, 12 wt % of $K_2O$, 5 wt % of MgO, 5 wt % of CaO, 4 wt % of $P_2O_5$ and 58 wt % of $SiO_2$ for the least bioactive composition.

The general composition of the U.S. Pat. No. 6,517,857B2 is provided on the table below:

TABLE

| Element | wt % |
| --- | --- |
| $SiO_2$ | 53-60 |
| $Na_2O$ | 0-34 |
| $K_2O$ | 1-20 |
| MgO | 0-5 |
| CaO | 5-25 |

TABLE-continued

| Element | wt % |
|---|---|
| $B_2O_3$ | 0-4 |
| $P_2O_5$ | 0.5-6 |

Subsequently, the fibers obtained undergo a surface treatment to increase reactivity. In this patent, the method used for obtaining these bioactive fibers is not specified, it is simply mentioned that the fibers were obtained per se. The tissue obtained has non-woven fibers, with smaller or larger pieces of fiber undergoing a spraying process in order to form the mesh while the fibers in this mesh have different diameters.

On this application, however, there is only one highly bioactive vitreous composition—which differs from the compositions used in the aforementioned patent—and because of this feature, it does not need any surface treatment to increase reactivity, which shortens processing steps, reducing costs and manufacturing time. The method used in this study to obtain bioactive fibers, the downdrawing, is the least expensive and the easiest processing method, thus leading to easy manufacturing of the present highly bioactive vitreous fabric.

Other differences are included in the composition, as shall be demonstrated in the present report.

The fiber obtained by the method used in the present application is continuous, not in pieces, ranging from millimeters to kilometers of extension, which eliminates the need, therefore, of using another technique to make the meshes and fabrics (as the spraying method in the aforementioned patent). The downdrawing machine enables the production of a non-woven fabric with or without orientation of the fibers and controlled porosity. The diameter of the fibers may also be the previously determined, allowing the choice of a single fixed diameter for the whole fabric or different fiber diameters.

U.S. Pat. No. 6,743,513B2 relates to the usage of bioactive glass and polymer layers for mechanical reinforcement of ductile metallic materials.

The published Brazilian patent document BR0605628A relates to the production of a hard, porous and bioactive ceramic matrix composed of alumina, hydroxylapatite and bioglass.

The published Brazilian patent document BR0900608A2 relates to the utilization of generic bioglass, with the same composition of the 45S5, and its crystallized version, using $NaPO_3$ as the exclusive source of phosphor, therefore, different from the object of this application.

The published Brazilian patent document BR0711988-7 relates to a vitreous composition for implant coating.

The international publication WO1995014127A1 discloses a composite that features bioactive glass fiber in its composition or ceramic fibers interspersed with structural fibers as carbon fibers in a polymeric matrix. This composite is applied in the coating of orthopedic implants. The composition of bioactive glass fibers is different from the composition object of this application, as well as the method to obtain the fibers (spinning) and their application.

And international publication WO1996021628A1 relates to a bioactive glass with the same range disclosed by U.S. Pat. No. 6,517,857B2, that is: $SiO_2$ 53-60 wt %; $Na_2O$ 0-34 wt %; $K_2O$ 1-20 wt %; MgO 0-5 wt %; CaO 5-25 wt %; $B_2O_3$ 0-4 wt %; $P_2O_5$ 0.5-6 wt %, therefore, different in composition and application regarding the research object of the Applicant that led to the present application.

SUMMARY OF THE INVENTION

In a broader sense, the composition of this invention is according to the Table below:

TABLE 1

| Element | Quantity in wt % |
|---|---|
| $SiO_2$ | 43-52 |
| $Na_2O$ | 4-9.5 |
| $K_2O$ | 20.5-32 |
| MgO | 0.5-2.5 |
| CaO | 15-20 |
| Au | 0.1-3.5 |
| Ag | 0.1-3.5 |
| $B_2O_3$ | 1.5-4 |
| $P_2O_5$ | 1-6 |
| ZnO | 0.1-3.5 |
| SrO | 0.1-3.5 |

The composition of Table 1 is processed through downdrawing, producing vitreous fibers, meshes and fabrics.

The vitreous composition and fabrics allow obtaining articles for varied applications in the medical and dental areas.

BRIEF DESCRIPTION OF THE DRAWINGS

FIG. 11 attached is a photograph of the test with a *Staphylococcus aureus* strain, image related to the first dilution.

DETAILED DESCRIPTION OF THE INVENTION

From a highly bioactive vitreous composition, continuous bioactive fibers are obtained with diameters controlled by the downdrawing process, as well as manufacturing of fibers in a highly bioactive, non-woven fabric, with oriented fibers and featuring certain porosity.

The bioactive vitreous composition object of this application allows for obtaining not only fibers, but also distinct forms of presentation, such as 3D structures, scaffolds (highly porous hard structures), meshes, fabrics and similar.

An aspect of the invention is the vitreous composition according to Table 1 below.

TABLE 1

| Element | Quantity in mol % | Quantity in wt % |
| --- | --- | --- |
| $SiO_2$ | 46-52 | 43-52 |
| $Na_2O$ | 5-10 | 4-9.5 |
| $K_2O$ | 15-32 | 20.5-32 |
| MgO | 0.5-2.5 | 0.5-2.5 |
| CaO | 15-20 | 15-20 |
| Au | 0.1-3.5 | 0.1-3.5 |
| Ag | 0.1-3.5 | 0.1-3.5 |
| $B_2O_3$ | 1.5-4 | 1.5-4 |
| $P_2O_5$ | 1.5-3 | 1-6 |
| ZnO | 0.1-3.5 | 0.1-3.5 |
| SrO | 0.1-3.5 | 0.1-3.5 |

Another aspect of the invention comprises the fibers obtained from said composition by downdrawing.

Yet another aspect are the articles obtained from fibers, including fibrous fabrics and scaffolds, and articles obtained from particulates, such as 3D structures obtained through 3D printing, various scaffolds and articles for medical and dental applications.

The use of vitreous formulations, which combine properties such as: rapid interaction with body fluids, that is, high bioactivity, and higher glass stability, with a broad working range, enables obtaining fibers through the downdrawing process.

The proposed composition of this invention confers increased reactivity to the glass and low chemical durability, as expected for a highly bioactive glass. Its greater higher glass stability allows the glass to be manipulated and to withstand thermal and/or sintering treatments, without presenting an uncontrolled crystallization, thus enabling simpler processes, that requires low crystallization tendency, to be used.

In order to maintain the vitreous fabric with its fibers oriented, a bioresorbable coating is applied. This coating may be composed of various bioresorbable polymers, but also, preferably, of a type I collagen thin layer that covers the surface of the fibers, providing support to the vitreous fabric and also protecting it against contact and reaction with air moisture.

Type I collagen is the most abundant protein in the human body, present in connective tissue, skin, tendons, bones, fibrous cartilage, etc. Besides, it is a widely known compound for initial assistance in tissue regeneration processes.

Figure 1:
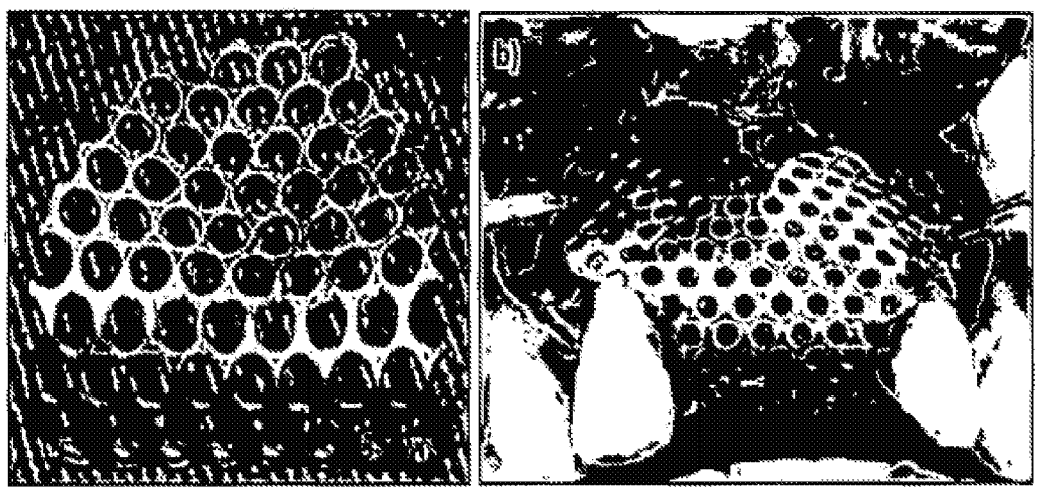
FIG. 1 attached is a picture that shows a) Titanium Mesh suitable for filling of orbital bone defect or dental application; and b) Titanium Mesh used in dental surgical procedure.
Figure 2:
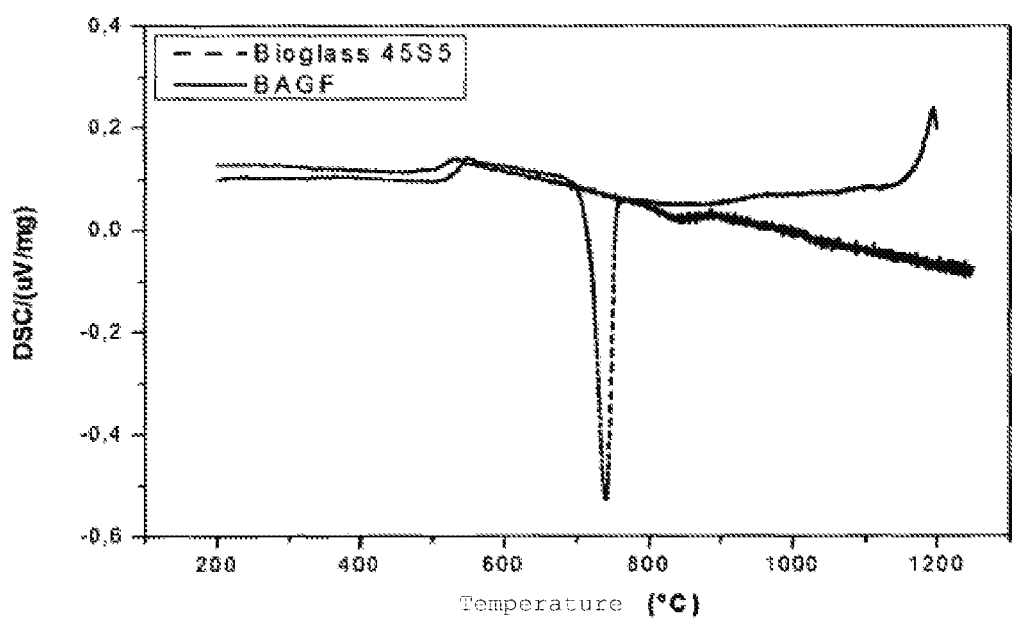
FIG. 2 attached is a chart obtained through a DSC testing with monolithic samples (average 20 mg) for formulation of 45S5 Bioglass (curve 1, control), and BAGF (curve 2, invention).

The formulation of the invention demonstrates outstanding results regarding stability, when tested via the Differential Scanning calorimetry technique (DSC) and does not show evident crystallization peaks when compared to the 45S5 formulation, as demonstrated in FIG. 2.

Figure 3A:
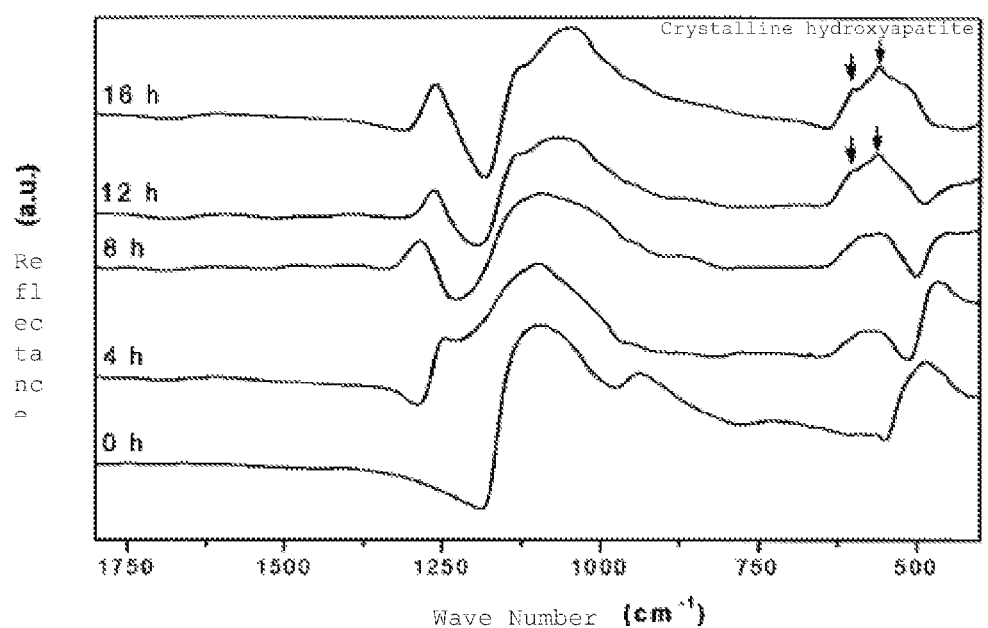
FIG. 3 attached is a chart obtained through FITR with the infrared spectrums of the glass bioactivity tests of BAGF formulation on 4 to 16 hour periods (FIG. 3A) and 24 to 168 hour periods (FIG. 3B).
Figure 3B:
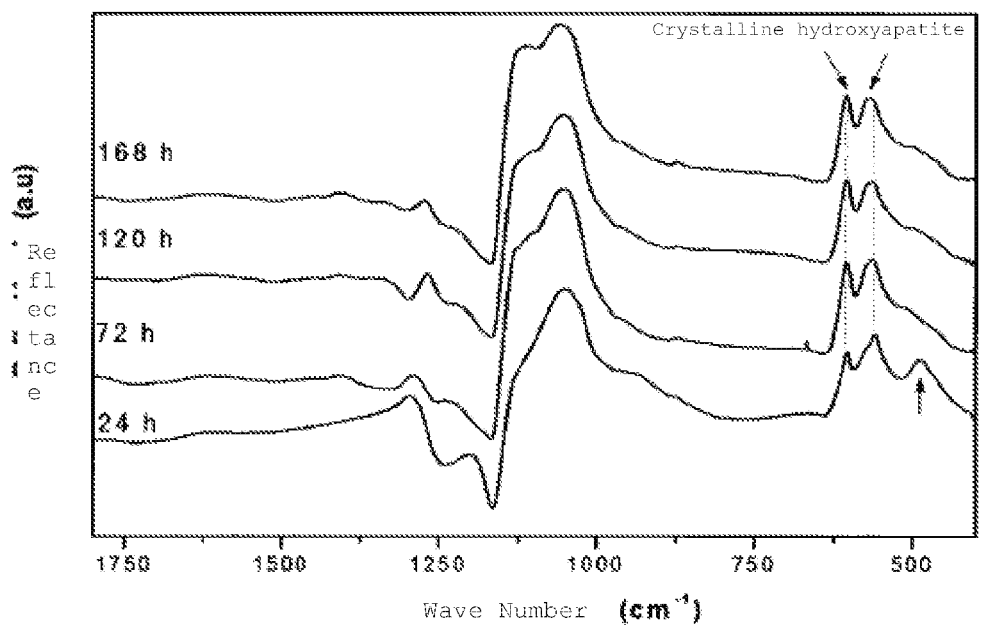

It also features outstanding bioactive properties when tested and analyzed in vitro using the SBF-K9 solution, forming the hydroxycarbonate apatite (HCA) layer in only 12 hours. FIGS. 3A and 3B show the curves obtained by the FTIR testing (Fourier Transform Infrared Spectroscopy), evidencing the formation of HCA after only 12 hours of testing in a solution for BAGF bioglass discs. The test was conducted from 4 to 168 hours of exposure of the BAGF glass to the solution.

Figure 4:
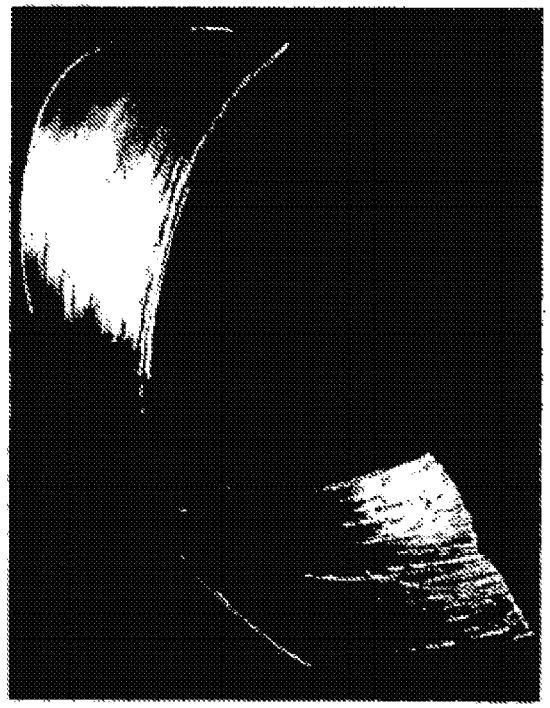
FIG. 4 attached is a photographic chart of a bioactive glass fiber fabric obtained through downdrawing of the composition of the invention.

From this composition, it was also possible to obtain fibers through downdrawing and also a vitreous fabric, as illustrated in FIG. 4.

The fiber obtained through the method of the invention is continuous and not fragmented, with a length ranging from millimeters to kilometers, obtained in a single step, thus, eliminating the need for additional techniques to obtain the fabric (such as spraying, as described in the aforementioned patent), since it is possible, to obtain non-woven fabrics with random or oriented fibers and controlled porosity with the downdrawing machine itself.

The articles manufactured from the fibers obtained through downdrawing may have the porosity ranging from 5 to 90%, depending on the arrangement of the fibers and whether bioresorbable polymers are used or not.

Furthermore, it is possible to previously determine the diameter of the fibers and choose if only a single fixed diameter is used for the entire fabric or different diameters, alternatively.

Via the downdrawing process, it is possible to obtain fibers with various diameters depending on rotation speed of the collecting drum. The diameters obtained range from 2 μm to 3 mm.

The downdrawing technique is consolidated and known for enabling the creation of glass fibers in industrial scale in a simple and inexpensive manner. In this technique, glasses in high temperature and adjusted viscosity may pass through orifices located at the bottom of crucibles or platinum devices (nozzles), thus forming filaments, which are quickly cooled, yielding the shape of fibers.

With the help of an X-ray Diffraction technique, information is collected about the crystals eventually formed when the machine is used, the average diameter of fibers and also definition of processing parameters such as heating rate, glass viscosity and drawing speed were defined throughout tests performed with the composition informed in Table 1, suitable for the fiber obtainment.

Figure 5:
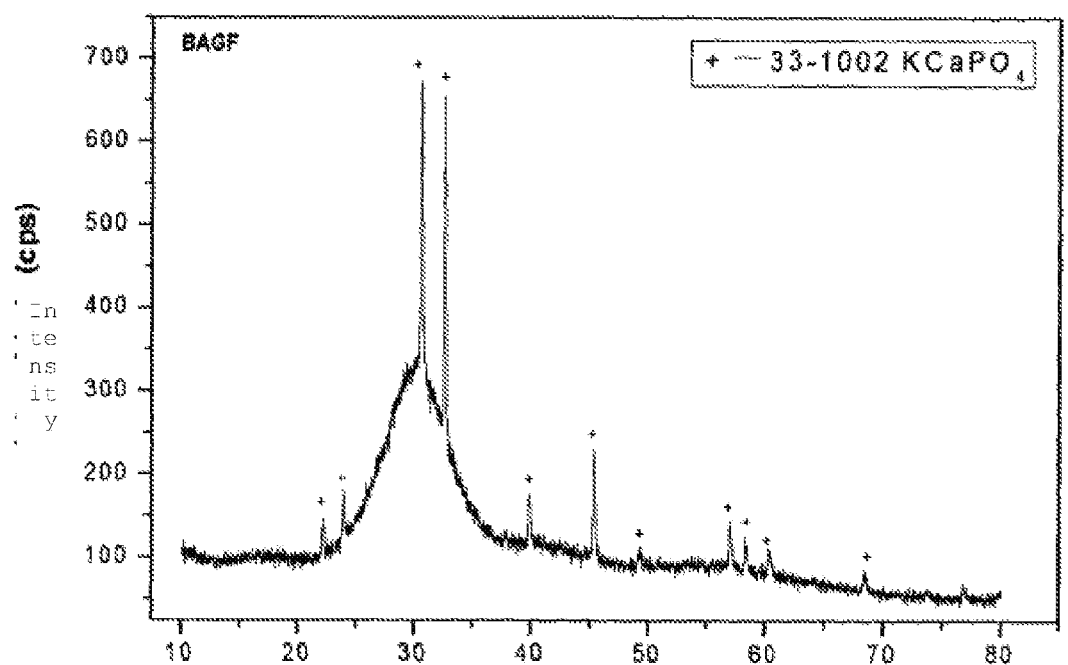
FIG. 5 attached is an X-ray diffractogram of the powdered sample of BAGF formulation using the thermal treatment for crystal growth at 700° C. for 120 minutes.

FIG. 5 shows the X-ray diffraction test, with a crystallized sample of the bioactive glass of the invention. A BAGF glass sample from the downdrawing machine (after 7 hours of processing) was treated in muffle at 700° C. for 120 minutes for growth and identification of crystals, which eventually are formed during the process. However, it should be remembered that the process is done in order for such event to be avoided, since it would affect obtaining the fibers via the downdrawing process. In spite of the great amount of amorphous material, the crystal $KCaPO_4$ was detected.

Figure 6:
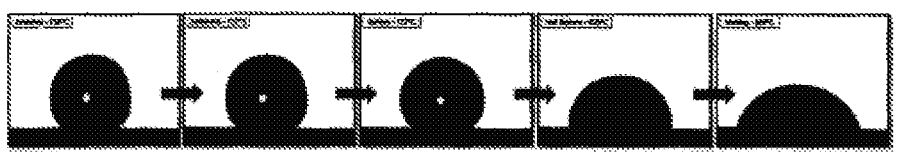
FIG. 6 attached are images obtained through the Heating Microscopy test for monolithic samples of the BAGF composition. Temperatures are: Sintering—708° C.; Softening—712° C.; Sphere—722° C.; Half-Sphere—820° C. and Meltdown—859° C.
Figure 7:
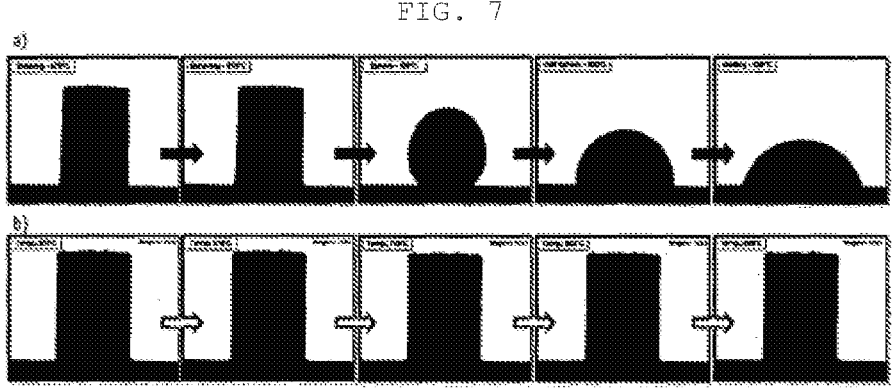
FIG. 7 attached are images obtained through the Heating Microscopy test for powdered samples of the BAGF and 45S5 Bioglass composition. Powder with particle size range between 25-75μ. a) BAGF with temperatures are: Sintering—575° C.; Softening—576° C.; Sphere—709° C.; Half-Sphere—802° C. and Meltdown—838° C. b) Bioglass 45S5 which does not feature these phases, since the powder cannot be sinterized due to crystallization.

Another test performed, which evidences the vitreous stability of the composition of the invention, is the heating microscopy technique (FIGS. 6 and 7), in which it was possible to observe that through the entire heating/cooling cycle, there was no crystal formation and the material was kept vitreous, which did not occur with the Bioglass 45S5, since it did not sintered due to the crystallization process.

Figure 8:
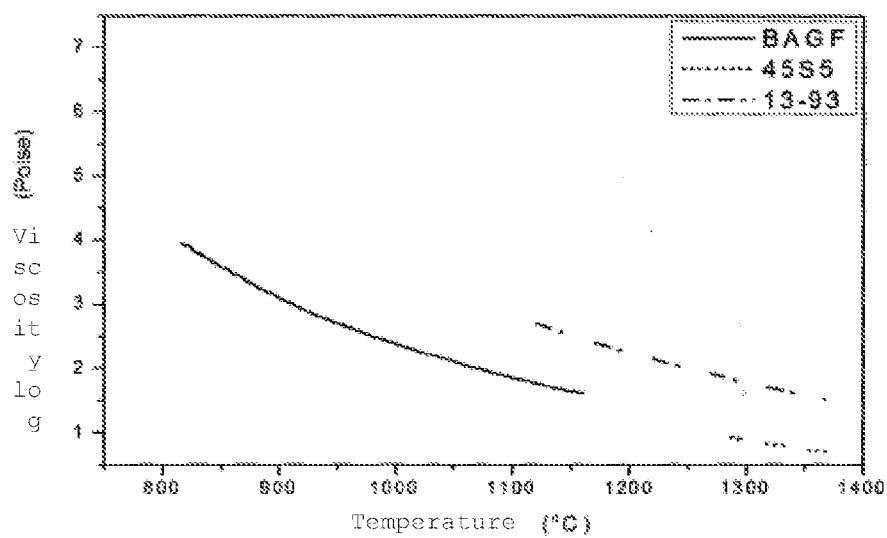
FIG. 8 attached is a viscosity chart expressed in Poise regarding the temperature for sampling of BAGF, 13-93 and 45S5.

FIG. 8 is a chart of the viscosity curve for the bioactive glass of the invention and for 13-93 and 45S5 bioactive glasses. In this chart, it may be once again observed that obtaining viscosity information for the Bioglass 45S5 is not possible on temperatures lower than 1200° C. due to the crystallization process that quickly takes place. Glass 13-93, on the other hand, was found to be more viscous than BAGF and this is due to the higher amount of silica in its formulation, but obtaining points from 1100° C. was also proven impossible due to the beginning of the crystallization process. Through this chart, it is possible to determine the working range temperature for the BAGF glass of the invention.

Various methods of application of a bioresorbable polymeric coating as well as different polymers were researched and proven to be applicable. The type I collagen is one of the biopolymers that demonstrated to have the necessary properties for coating this vitreous fiber fabric and it also takes part in various reactions of tissue regeneration and healing.

In order to obtain bioactive fibers by the downdrawing process, a certain amount of bioactive glass, in a monolithic form that results from the melting process of the mixture of raw materials in an furnace with 1000-1350° C. temperature, is heated within the downdrawing machine furnace until its melts completely, in a temperature ranging from 1000-1250° C.

Subsequently, the temperature of the furnace is decreased to 700-950° C., for adjustment of the viscosity of the cast material, obtaining a vitreous mass with viscosity between $10^{4.0}$ and $10^{2.5}$ Poise. This viscosity range is considered ideal for obtaining fibers in industrial scale, while keeping the furnace temperature, at least, 20 Celsius degrees above the liquidus temperature.

During the drawing process, the selected coating may be applied simultaneously, with the help of an applier device. Thus, fibers are coated with the polymer and, subsequently, collected by a controlled rotation drum, enabling a precise control of their obtained diameters.

The thickness of the coating may also be controlled, with a scale ranging from nanometers to millimeters (thicknesses equal or higher than 250 nanometers more precisely).

The vitreous fabric is obtained simultaneously to the collection of bioactive glass fibers. The fabric is manufactured in a device coupled to the downdrawing machine.

The thickness of the vitreous fabric, as well as the interlacing between fibers may be controlled with the help of devices present in the machine and through variation of the colleting times of fiber.

Vitreous fabrics can be obtained with a single fiber layer, therefore from 2 μm, until multiple layers, reaching up to centimeters in thickness. The optimal working range for vitreous fabrics with extremely high flexibility and rapid degradation rate is from 0.05 mm to 1 mm thickness.

In summary, the thickness of the vitreous fabric, fiber diameter, thickness of the coating may vary and be adjusted depending on the desired application for the final product. These, among other characteristics of the product, shall grant control of the degradation rate both of the polymer and the bioactive glass for in vitro and in vivo procedures.

These vitreous fabrics were tested in vitro using osteoblasts. Cell viability assays were performed and the developed glass presented very favorable and similar results to the standard market Bioglass45S5. That is, the bioactive glass of the invention enables adhesion and viability of bone tissue cells as well as the golden standard Bioglass 45S5.

Figure 9:
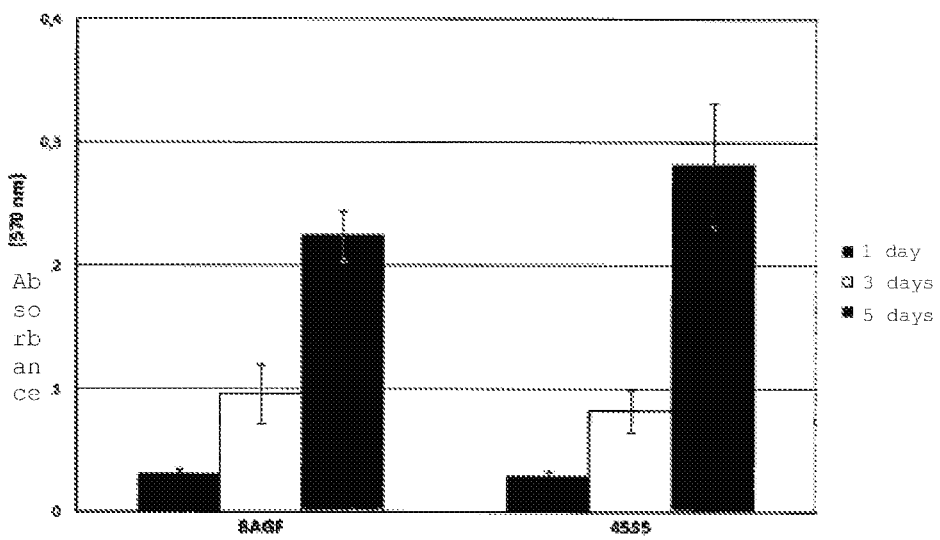
FIG. 9 attached is a bar chart showing a cell viability assay (MTT) of UMR 106 osteoblasts within periods of 1, 3 and 5 days (data with no statistic difference).
Figure 10:
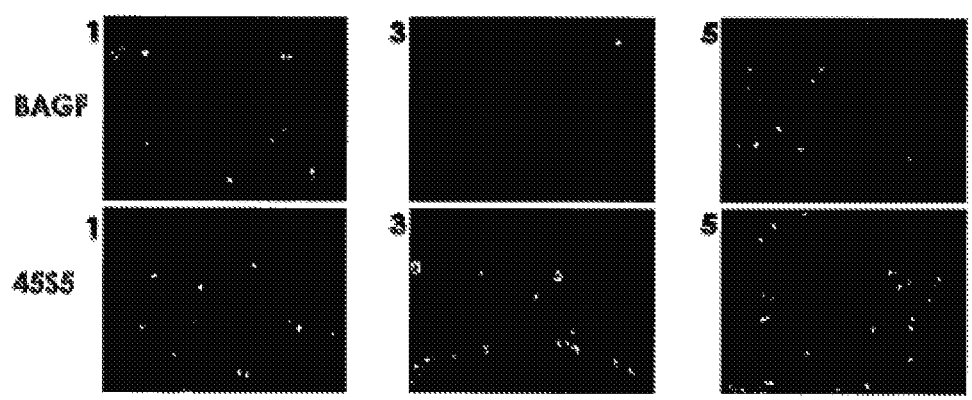
FIG. 10 attached shows the Micrographs corresponding to the cell viability assay (MTT) of UMR 106 osteoblasts within periods of 1, 3 and 5 days.

Results may be observed on FIGS. 9 and 10.

Antibacterial Properties

Essays for verification of antibacterial capacity of the new vitreous composition and fabrics were conducted following the guidelines of JIS 2801:2010 and ISO 22196:2011 standards. The tests used *E. coli* and *Staphylococcus aureus* strains.

Figure 11A:
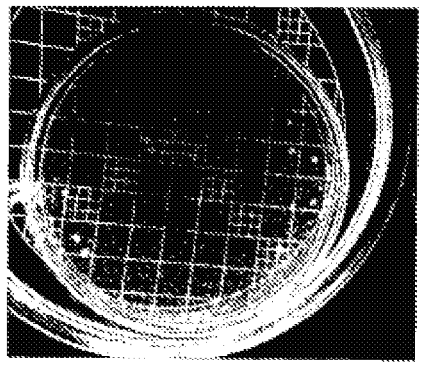
FIG. 11A: Control (window glass only)
Figure 11B:
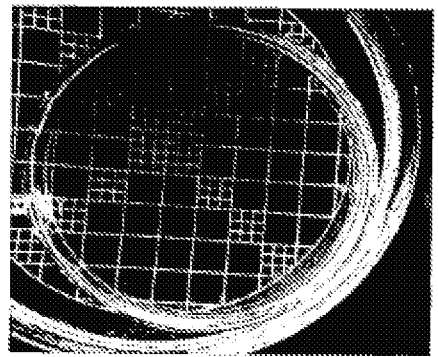
FIG. 11B: Bioactive fabric of the invention.

The material was capable of interacting and eliminating viable colony forming units in both strains, in all dilutions and, therefore, it has antibacterial (bactericide) properties as demonstrated by FIG. 11. FIG. 11A is the control sample (window glass), with countless colony forming units (CFU)

and FIG. 11B is the vitreous composition sample of the invention (BAGF) with no CFU.

Cytotoxicity Assays

Cytotoxicity assays (MTT) were performed with L929 fibroblasts, as well as OSTEO-1 osteoblasts with experimental times of 24, 72 and 144 hours for dilutions obtained from the submerged material in DMEM (Dulbeco's Modified Eagle Medium) culture medium, being 100% the solution directly extracted from the submerged material and percentages presented, dilutions arising from this solution. The results are shown in FIG. 12 and FIG. 13.

Figure 12:
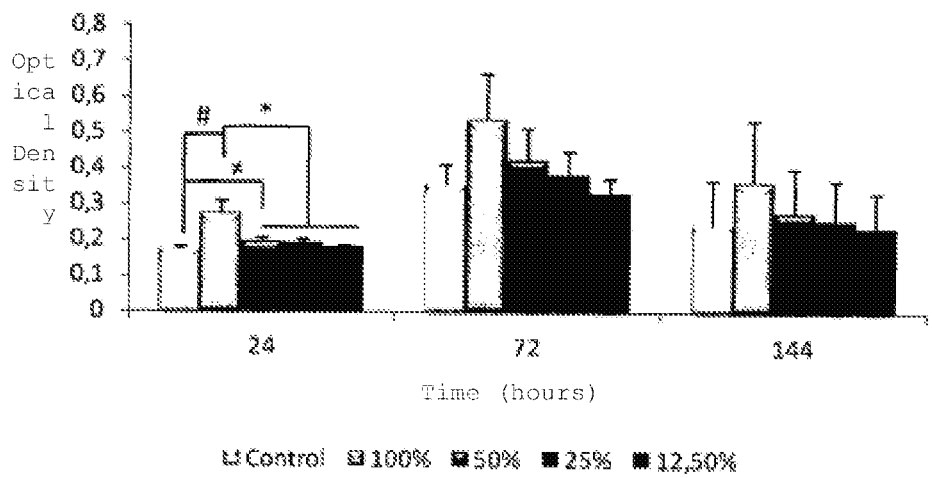
FIG. 12 attached shows a bar chart of the cell proliferation of fibroblasts in different dilutions of the extract obtained through submersion of the bioactive tissue in a DMEM medium (100%, 50%, 25% and 12.5%), with (#)$p<0.05$ versus CG, (≠)$p<0.05$ versus CG, and (*)$p<0.05$ versus 50%, 25% and 2.5%.
Figure 13:
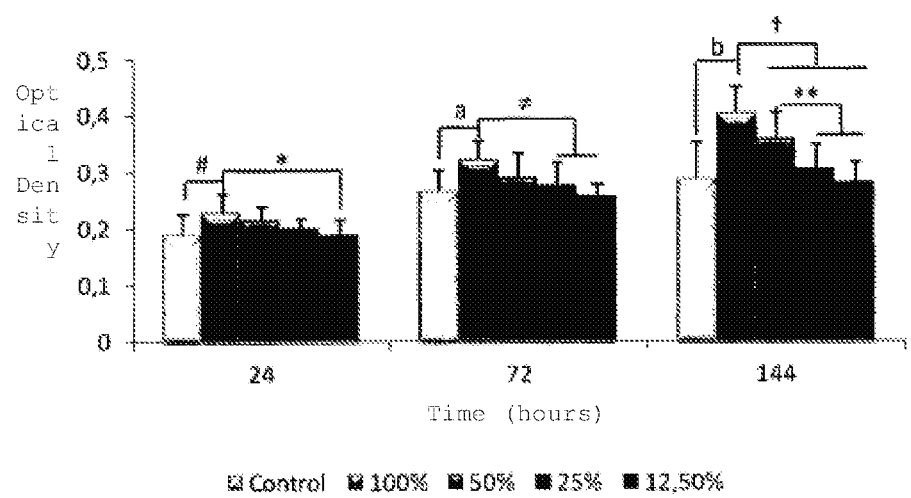
FIG. 13 attached shows a bar chart of osteoblast cell proliferation in different dilutions of the extract obtained through submersion of the bioactive fabric in a DMEM medium (100%, 50%, 25% and 12.5%), with (#)$p<0.05$ versus CG, (*)$p<0.05$ versus 12.5%, (a)$p<0.05$ versus CG, (≠)$p<0.05$ versus 25% and 12.5%, (b)$p<0.05$ versus CG, (†)$p<0.05$ versus 50%, 25% and 12.5%, and (**)$p<0.05$ versus 25% and 12.5%.

The tests shown in FIGS. 12 and 13 present the higher level of cell proliferation either for fibroblasts or osteoblasts, particularly in the 100% group. It indicates cell metabolism acceleration with respect to the control group and evidences the non-cytotoxicity of the new bioactive glass material.

In Vivo Results

In vivo tests were performed in order to assess the genotoxicity, cytotoxicity and verification of the aid towards the tissue regenerative capacity of the invention biomaterial.

Genotoxicity Assay

Comet Assay II tests were performed for fibroblasts and osteoblasts from samples implemented subcutaneously in the dorsal of Wistar rats, in the periods of 15, 30 and 60 days.

Figure 14:
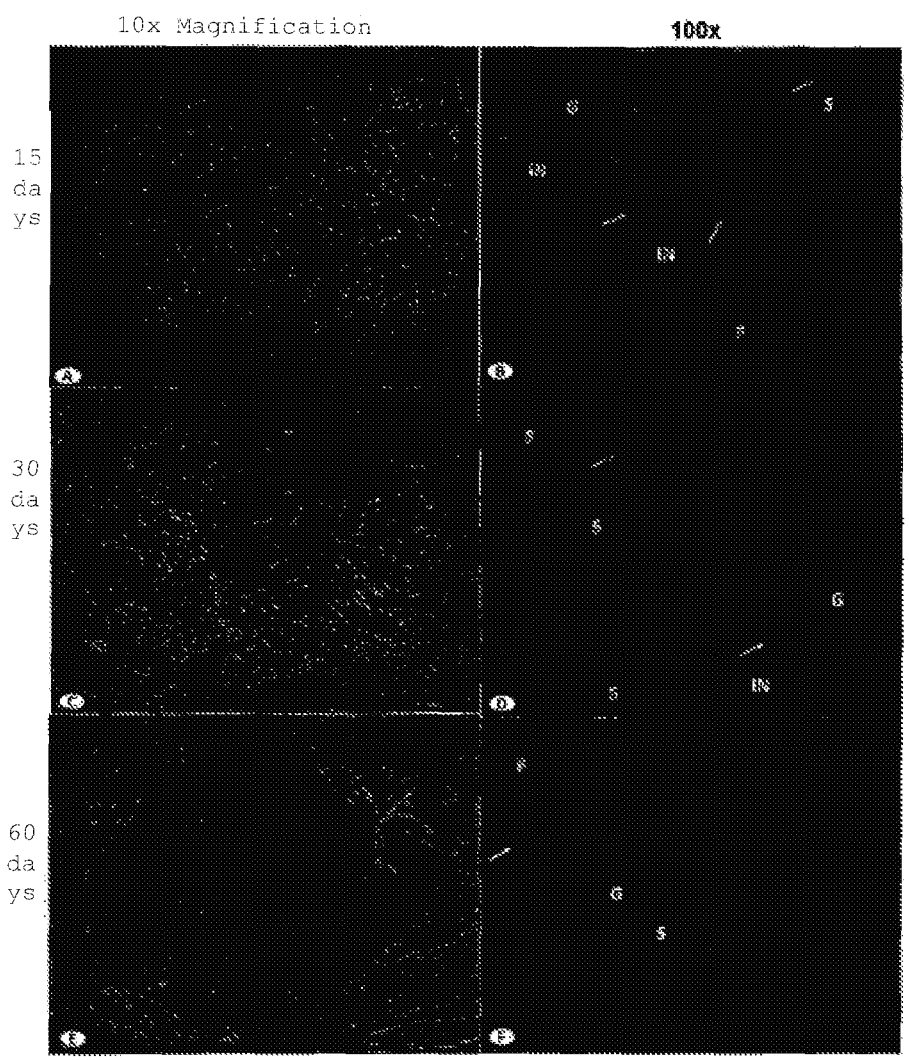
FIG. 14 attached shows histological sections of the subcutaneous implant colored with Hematoxylin-Eosin for experimental periods of 15 (A-B), 30 (C-D) and 60 days (E-F). Scale bars represent 1 mm for a 10× magnification. Inflammatory Cells (IN), Granulation Tissue (G), Bioactive Glass Fibers (S), Fibrous Capsule (F) and Multinuclear Giant Cells. Scale bars represent 100 μm for a 100× magnification.

From this test and histological analysis, it was possible to verify the absence of any damage to the cells genetic code and the material provided the growth of an organized tissue without the presence of a fibrous capsule. The material showed to be reabsorbable, as appears in FIG. 14.

Figure 15:
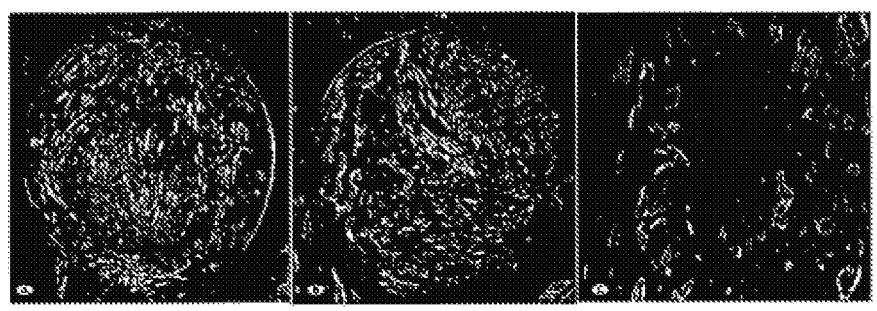
FIG. 15 attached shows the histological analysis of a tibial lesion in periods of 15 (A), 30 (B) and 60 days (C). Scale bars represent 1 mm for a 10× magnification. Material: prepared scaffold from fibers obtained through downdrawing. The fibers were implanted on 3 mm defects of rat tibias.
Figure 16:
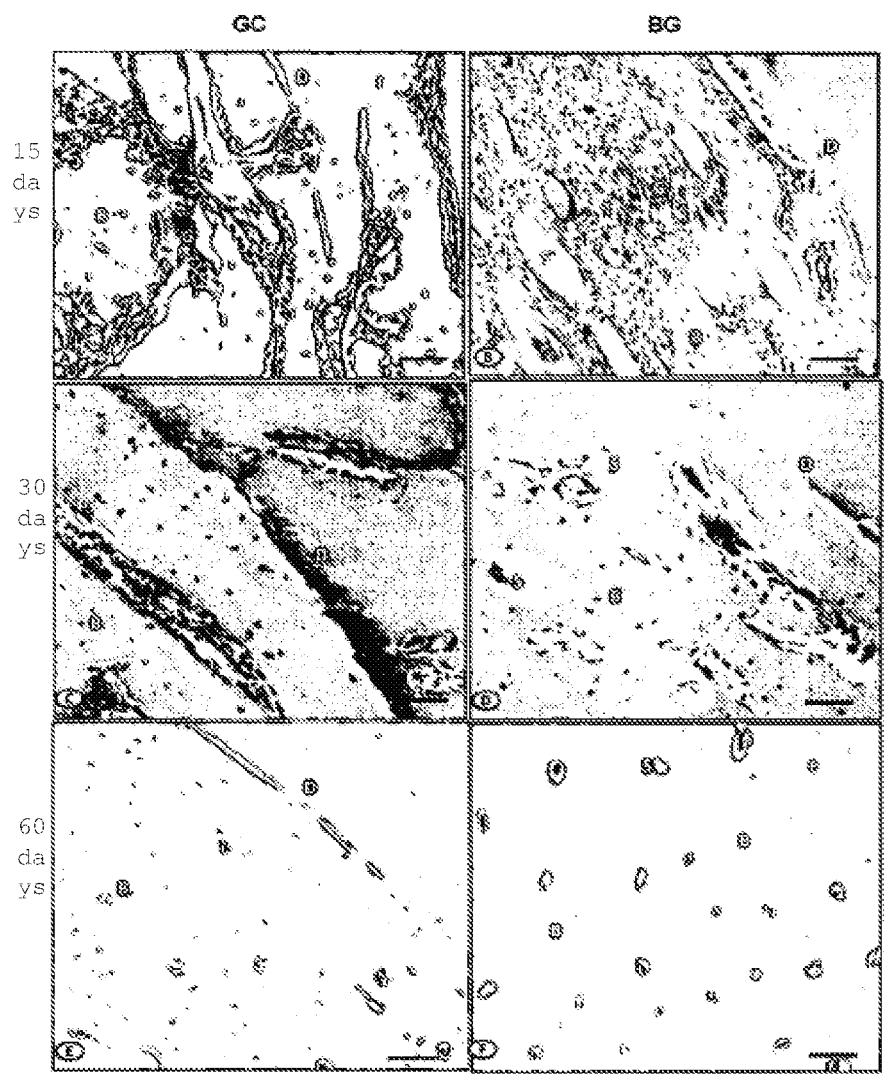
FIG. 16 attached shows histological sections of the tibial lesion colored with Hematoxylin-Eosin for groups GC (Control Group) and BG (group treated with the biomaterial of the invention) for the experimental periods of 15 (A-B), 30 (C-D), and 60 days (E-F). Inflammatory Cells (IN), Granulation Tissue (G), Bioactive Glass Fibers (S), Fibrous Capsule (F) and Multinuclear Giant Cells, Bone Neoformation (B) and Rim of the Lesion (D). Scale bars represent 100 μm for a 100× magnification.

In bone regeneration applications, the material presented a similar reabsorbing rate to the new bone formation in 3 mm diameter tibial defects in 60 Wistar rats. The experimental times chosen were 15, 30 and 60 days. Results also indicate that the material stimulate new bone formation as presented in FIGS. 15 and 16.

Figure 17:
FIG. 17 attached shows an image obtained during the surgical procedure for implanting the material of the invention on a 6 mm defect on the cranial bone of Wistar rats.

Essays identifying the BAGF capacity of bone regeneration in rat calvarial defects were also carried out. Bone defects with 6 mm diameter were made on the cranial bone of 48 animals (Wistar rats). FIG. 17 shows the surgical procedure with the implementation of the bioactive glass fibers obtained by downdrawing.

Figure 18:
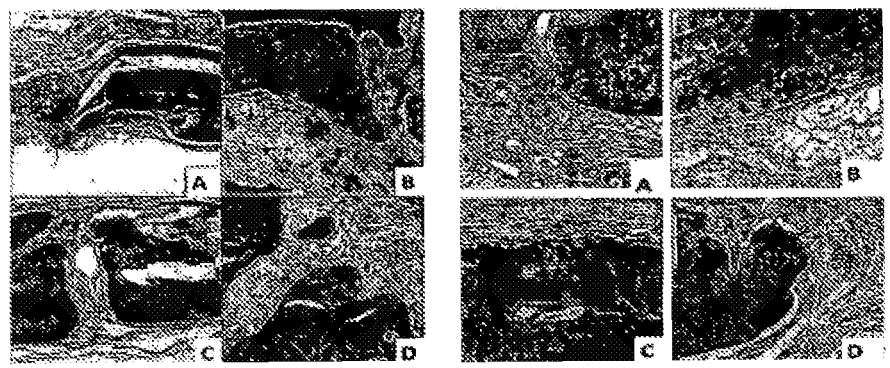
FIG. 18 attached shows the results obtained through histological sections colored with Hematoxylin-Eosin for control groups (a) and BAGF treated (b) for 2, 4, 8 and 16 weeks.

FIG. 18 shows the results obtained from this study. Animals treated with the invention biomaterial had the formation of a more organized hard tissue, with quite accelerated growth when compared to the control group (without the invention material) and the material's degradation rate accompanying the tissue regeneration process may be once again verified, indicating that the material degrades at an approximate rate as the tissue regeneration.

Figure 19:
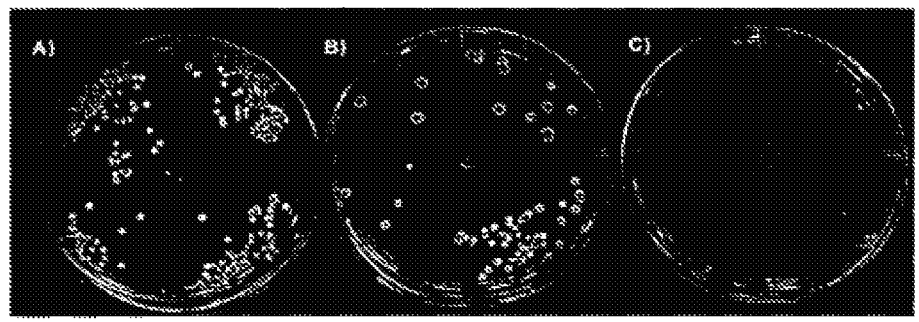
FIG. 19 attached illustrates the analysis for verification of elimination of biofilm on the $4^{th}$ and $5^{th}$ dilutions, after 24 h. A) Window glass; B) Bioglass 45S5 and C) bioactive composition of the invention (BAGF).

In addition to FIG. 11 concerning the antimicrobial activity of the invention bioactive material, FIGS. 19 and 20 as follows also show that the vitreous bioactive composition of the invention, as well as the products from its dissolution (ions dissolved in the medium) show antibacterial and antifungal properties.

The bioactive materials of the invention having antimicrobial properties are useful at the cosmetics-pharmaceutical, agricultural or food areas, civil construction industry, paper, textile and environment areas, without limitation thereto.

At first, in order to reach such properties, the material may be used under different presentation formats, such as powder, granules or porous or non-porous 3D pieces.

The elimination of biofilm capability, a feature that does not usually occur in materials, such as glass and other, is fully achieved with the invention material, as shown in experiments from FIG. 9. FIGS. 19A and 19B show control materials, in $4^{th}$ and $5^{th}$ dilutions, which formed biofilm when tested under the conditions provided at the test. The test may be inquired in Brazilian Dental Journal (2014) 25, available at http://dx.doi.Org/10.1590/0 03-6440201302398.

However, the glass prepared from the invention material, FIG. 19C, does not show any formation of biofilm, since it has antibacterial/antifungal properties.

Figure 20:
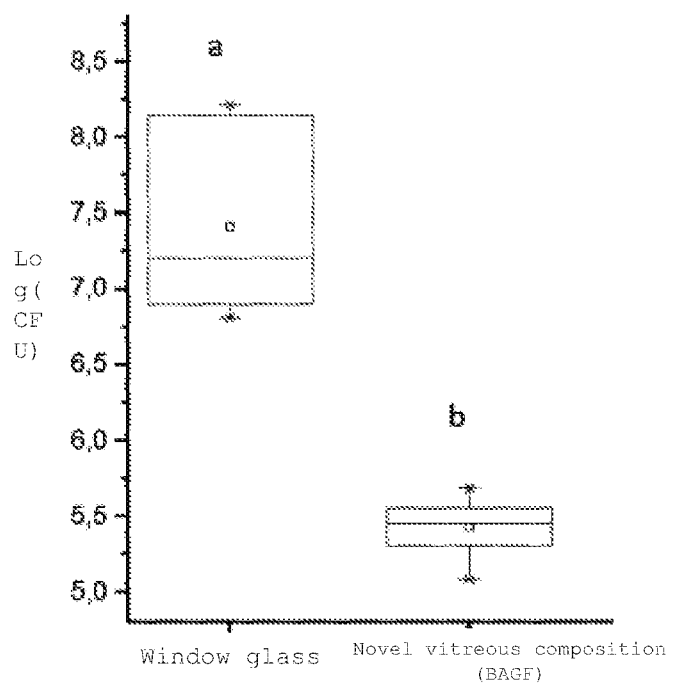
FIG. 20 attached is a chart that illustrates the analysis for verification of elimination of biofilm after 72 h. Results for window glass and for the bioactive composition of the invention (BAGF).

FIG. 20 also shows the biofilm elimination capacity after 72 hours, very higher than that from any control material under the same testing conditions.

Therefore, the fabric developed enables a great advance in the tissue engineering field, since this biomaterial may be applied as a graft in order to aid healing and in situ regeneration processes for different human body tissues, as well as in in vitro-tissue engineering processes.

Its application and manipulation also show an advantage with respect to other alloplastic materials, since it has flexibility and can adjust itself to different fracture contours, bone cavity or injury from different tissues.

Other clear advantage is that in grafting procedures this fibers or fabrics can decrease surgical steps, since this material is reabsorbable and, therefore, it does not require any further removal, diminishing patient's discomfort, contamination risk and the total procedure cost.

The vitreous fabrics developed are classified as third generation biomaterials and show a broad applicability. They can be applied in hard tissue regeneration, skin wound healing and in soft tissue regeneration in medical and dental procedures.

In other presentation forms, this vitreous composition may also be used as scaffolds and granules for bone regeneration and as powder of different granulometric ranges may be used for remineralization of dental tissues after chemical erosion or teeth whitening.

In the following, several methods of usage for this new biomaterial are presented.

- As powder with granulometric range from 1-10 μm for tooth enamel remineralization, after chemical or mechanical erosive procedures and teeth whitening as well.
- As powder with granulometric range from 1-25 μm for obliteration of dentinal tubules for dentin hypersensitivity treatments.
- As particulates with granulometric range from 60-700 μm for bone regeneration on dental grafting procedures for periodontal disease recovery.
- As particulates with granulometric range from 100 μm-1.5 mm for grafting procedures, on dental implant pre-procedure, for grafting on oral-maxillofacial procedures and treatment of grafting under traumatic conditions.
- As vitreous fabric on orthopedic procedures, traumatic post-conditions, such as bone fractures.
- As vitreous fabric on medical and dental procedures requiring mesh, tissues or membranes for rehabilitation or containment of other alloplastic, xenogenous or autogenous material.
- As vitreous fabric or mesh operating as a membrane for hard and/or soft tissue regeneration guide.

As vitreous fabric to replace the titanium mesh, since it requires to be removed after the osseous consolidation, as this tissue is reabsorbable, not requiring the second surgical step.

As vitreous fabric in using wound pads, which may be applied for skin wound regeneration, either in perfectly healthy patients or patients having poor skin regeneration due to any illness, such as type I or II diabetes, osteoporosis, etc.

As vitreous fabric for skin burn regeneration and protection.

As vitreous fabric for the regeneration of chondrocytes, that is, cartilaginous tissue.

As scaffolds manufactured from a tangle of fibers either dipped or not in a highly porous polymer matrix or also synthesized from powder, for bone regeneration in procedures that do not require any load support, that is, do not require high mechanical strength of the material.

As fabric in first-aid or surgical procedures requiring grafts and/or plasters with antimicrobial properties.

The invention claimed is:

1. A vitreous composition comprising the elements in wt % ranges according to Table I:

TABLE I

| Element | Quantity in wt % |
|---|---|
| $SiO_2$ | 43-52 |
| $Na_2O$ | 4-9.5 |
| $K_2O$ | 20.5-32 |
| MgO | 0.5-2.5 |
| CaO | 15-20 |
| Au | 0.1-3.5 |
| Ag | 0.1-3.5 |
| $B_2O_3$ | 1.5-4 |
| $P_2O_5$ | 1-6 |
| ZnO | 0.1-3.5 |
| SrO | 0.1-3.5. |

2. The vitreous composition according to claim 1, wherein when the composition in a bulk form is subject to a simulated body fluid (SBF) in vitro a hydroxyapatite (HCA) layer is formed within 12 hours.

3. The vitreous composition according to claim 1, wherein the composition comprises a distribution powder with particle sizes between 1-10 μm.

4. The vitreous composition according to claim 1, wherein the composition comprises a distribution powder with particle sizes between 1-25 μm.

5. The vitreous composition according to claim 1, wherein the composition comprises antifungal and antimicrobial properties.

6. The vitreous composition according to claim 1, wherein the composition comprises a distribution particulate with particle sizes between 60-700 μm.

7. The vitreous composition according to claim 1, wherein the composition comprises a distribution particulate with particle sizes between 100 μm-1.5 mm.

8. A vitreous fiber prepared from the composition according to claim 1 prepared by a process comprising:
heating the composition of claim 1 to between 1000-1250° C;
decreasing the temperature to between 700-950° C;
maintaining the temperature at least 20° C. higher than the liquidus temperature of the composition;
obtaining a vitreous mass with viscosity from between $10^{4.0}$ to $10^{2.5}$ Poise; and
pulling the vitreous mass while simultaneously applying a collagen I coating.

9. The vitreous fiber according to claim 8, wherein the collagen I coating has a thickness of at least 250 nanometers.

10. The vitreous fiber according to claim 8, wherein the fiber has length from between at least 1 millimeter to at least 1 kilometer.

11. The vitreous fiber according to claim 8, wherein the fiber has a diameter from between 2 μm to 3 mm.

12. The vitreous fiber according to claim 8, wherein heating the composition of claim 1 to between 1000-1250° C. comprises heating the composition of claim 1 to between 1000-1250° C. in downdrawing machine furnace.

13. The vitreous fiber according to claim 8 prepared by a process further comprising collecting the vitreous fiber through a controlled rotating drum.

14. A vitreous fabric and mesh prepared from the vitreous fiber according to claim 8 comprising a porosity of between 5 and 90%.

15. The vitreous fabric according to claim 14, wherein the fabric has a thickness of at least 2 μm (0.002 mm).

16. The vitreous fabric according to claim 15, wherein the fabric has a thickness of between 0.05 mm and 1 mm.

17. An article prepared from the vitreous composition according to claim 1 prepared by a process comprising:
providing a particulate form of the vitreous composition; and
optionally subjecting the particulate to a sintering processes.

18. The article according to claim 17 prepared by a process further comprising processing the particulate in a 3D printer.

19. The article according to claim 17, wherein the article is selected from the group consisting of 3D pieces and scaffolds.

20. The article according to claim 17, wherein the article comprises a distribution particulate with particle sizes between 60-700 μm.

21. The article according to claim 17, wherein the article comprises a distribution particulate with particle sizes between 100 μm-1.5 mm.

22. The article according to claim 17, wherein the article comprises a tangle of fibers either in a polymer or non-polymer matrix.

* * * * *